United States Patent
Skahan et al.

(10) Patent No.: US 9,327,119 B2
(45) Date of Patent: May 3, 2016

(54) ELECTROSTIMULATION SYSTEM

(75) Inventors: Michael S. Skahan, Escondido, CA (US); Kevin R. Lunau, Valley Center, CA (US); David K. Combs, Oceanside, CA (US); Wallace Ray Fischer, Amesville, OH (US)

(73) Assignee: VISION QUEST INDUSTRIES INCORPORATED, Irvine, CA (US)

( * ) Notice: Subject to any disclaimer, the term of this patent is extended or adjusted under 35 U.S.C. 154(b) by 12 days.

(21) Appl. No.: 14/234,984

(22) PCT Filed: Jul. 27, 2012

(86) PCT No.: PCT/US2012/048625
§ 371 (c)(1),
(2), (4) Date: Jan. 24, 2014

(87) PCT Pub. No.: WO2013/016664
PCT Pub. Date: Jan. 31, 2013

(65) Prior Publication Data
US 2014/0155799 A1 Jun. 5, 2014

Related U.S. Application Data

(60) Provisional application No. 61/512,402, filed on Jul. 27, 2011, provisional application No. 61/576,342, filed on Dec. 15, 2011.

(51) Int. Cl.
*A61B 5/04* (2006.01)
*A61N 1/00* (2006.01)
(Continued)

(52) U.S. Cl.
CPC .......... *A61N 1/36021* (2013.01); *A61F 5/0123* (2013.01); *A61N 1/0408* (2013.01); *A61N 1/0484* (2013.01); *A61N 1/37247* (2013.01); *A61N 1/205* (2013.01); *A61N 1/22* (2013.01)

(58) Field of Classification Search
USPC .......................................... 607/149; 600/372
See application file for complete search history.

(56) References Cited

U.S. PATENT DOCUMENTS 1,745,446 A  2/1930  Payne
3,911,910 A  10/1975  Oesau et al.
(Continued)

FOREIGN PATENT DOCUMENTS

DE  20116887 U1  4/2002
WO  9843560 A1  10/1998
(Continued)

OTHER PUBLICATIONS

Zizic TM, The treatment of osteoarthritis of the knee with pulsed electrical stimulation. J Rheumatol. 1995;22:1757-1761.
(Continued)

*Primary Examiner* — Nicole F Lavert
(74) *Attorney, Agent, or Firm* — Lawrence N. Ginsberg

(57) ABSTRACT

An electrostimulation system of the invention includes a signal generator, a docking assembly, and at least one transmission assembly. The signal generator is configured to produce at least one signal. The docking assembly includes a main housing; at least one mechanical retaining element operatively connected to the main housing that mechanically secures the signal generator to the docking assembly; and, at least one electrical docking element mechanically connected to the main housing that electrically connects the docking assembly to the signal generator. The at least one transmission assembly is adapted to fit on a portion of a user's anatomy, including at least one transmission assembly connection element (TACE) adapted to transmit a signal from the docking assembly to the user. The signal generator is electrically and mechanically detachably connected to the docking assembly during use.

17 Claims, 14 Drawing Sheets

(51) Int. Cl.
*A61N 1/36* (2006.01)
*A61N 1/04* (2006.01)
*A61F 5/01* (2006.01)
*A61N 1/372* (2006.01)
*A61N 1/20* (2006.01)
*A61N 1/22* (2006.01)

(56) References Cited

U.S. PATENT DOCUMENTS

| | | |
|---|---|---|
| 4,271,831 A | 6/1981 | Deibert |
| 4,467,809 A | 8/1984 | Brighton |
| 4,487,834 A | 12/1984 | Brighton et al. |
| 4,554,923 A | 11/1985 | Batters |
| 4,586,495 A | 5/1986 | Petrofsky |
| 4,686,969 A | 8/1987 | Scott |
| 4,759,368 A | 7/1988 | Spanton et al. |
| 4,796,631 A | 1/1989 | Grigoryev et al. |
| 4,832,033 A | 5/1989 | Maher et al. |
| 4,872,448 A | 10/1989 | Johnson, Jr. |
| 4,917,092 A | 4/1990 | Todd et al. |
| 4,938,207 A | 7/1990 | Vargo |
| 5,014,699 A | 5/1991 | Pollack et al. |
| 5,215,100 A | 6/1993 | Spitz et al. |
| 5,230,697 A | 7/1993 | Castillo et al. |
| 5,273,033 A | 12/1993 | Hoffman |
| 5,277,698 A | 1/1994 | Taylor et al. |
| 5,288,287 A | 2/1994 | Castillo et al. |
| 5,316,547 A | 5/1994 | Gildersleeve |
| 5,374,283 A | 12/1994 | Flick |
| 5,542,911 A | 8/1996 | Cassford et al. |
| 5,628,722 A | 5/1997 | Solomonow |
| 5,645,524 A | 7/1997 | Doyle |
| 5,974,344 A | 10/1999 | Shoemaker et al. |
| 6,064,911 A | 5/2000 | Wingrove |
| 6,064,912 A | 5/2000 | Kenney et al. |
| 6,110,135 A | 8/2000 | Madow et al. |
| 6,121,508 A | 9/2000 | Bischof et al. |
| 6,329,161 B1 | 12/2001 | Heller |
| 6,344,021 B1 | 2/2002 | Juster |
| 6,436,066 B1 | 8/2002 | Lockhart |
| 6,456,884 B1 | 9/2002 | Kenney |
| 6,477,410 B1 | 11/2002 | Henley et al. |
| 6,792,313 B2 | 9/2004 | Nachum |
| 6,904,614 B2 | 6/2005 | Yamazaki et al. |
| 7,022,506 B2 | 4/2006 | Brighton et al. |
| 7,130,692 B2 | 10/2006 | Brighton et al. |
| 7,158,835 B2 | 1/2007 | Brighton et al. |
| 7,167,753 B2 | 1/2007 | Brighton et al. |
| 7,215,995 B2 | 5/2007 | Brighton et al. |
| 7,354,748 B2 | 4/2008 | Brighton |
| 7,465,546 B2 | 12/2008 | Brighton |
| 7,468,264 B2 | 12/2008 | Brighton et al. |
| 7,628,750 B2 | 12/2009 | Cohen et al. |
| 7,957,816 B2 | 6/2011 | Monogue et al. |
| 8,209,030 B2 | 6/2012 | Minogue et al. |
| 2002/0072664 A1 | 6/2002 | Katzenmaier et al. |
| 2002/0165590 A1 | 11/2002 | Crowe et al. |
| 2002/0188229 A1 | 12/2002 | Ryaby et al. |
| 2002/0198475 A1 | 12/2002 | Elias |
| 2003/0114896 A1 | 6/2003 | Boute et al. |
| 2003/0153848 A1 | 8/2003 | Talish et al. |
| 2003/0187375 A1 | 10/2003 | Gaylord |
| 2004/0015208 A1 | 1/2004 | Haugland et al. |
| 2004/0162593 A1 | 8/2004 | Jorgenson et al. |
| 2004/0267333 A1 | 12/2004 | Kronberg |
| 2005/0087148 A1 | 4/2005 | Rabello |
| 2005/0278001 A1 | 12/2005 | Qin et al. |
| 2006/0135896 A1 | 6/2006 | Latimer |
| 2006/0190043 A1 | 8/2006 | Brighton et al. |
| 2006/0293724 A1 | 12/2006 | Kronberg et al. |
| 2007/0038252 A1 | 2/2007 | Carroll |
| 2007/0112394 A1 | 5/2007 | Nathan et al. |
| 2007/0118965 A1 | 5/2007 | Hoffman |
| 2007/0173895 A1 | 7/2007 | Reichenbach |
| 2007/0191912 A1 | 8/2007 | Fischer et al. |
| 2007/0299472 A1 | 12/2007 | Brighton |
| 2008/0281392 A1 | 11/2008 | Paolizzi et al. |
| 2009/0182394 A1* | 7/2009 | Bachinski ............... 607/59 |
| 2009/0287126 A1 | 11/2009 | Skahan et al. |
| 2010/0082079 A1 | 4/2010 | Skahan et al. |
| 2011/0213295 A1 | 9/2011 | Henley et al. |

FOREIGN PATENT DOCUMENTS

| | | |
|---|---|---|
| WO | 02060311 A2 | 8/2002 |
| WO | 02060311 A3 | 12/2002 |
| WO | 2004098703 A2 | 11/2004 |
| WO | 2005049132 A1 | 6/2005 |
| WO | 2007019569 A2 | 2/2007 |
| WO | 2007019569 A3 | 10/2007 |
| WO | 2008137319 A1 | 11/2008 |

OTHER PUBLICATIONS

Electrical Stimulation helps delay knee replacement surgery. Mont MA, Hungerford DS, Caldwell JR, Hoffman KC, Zizic TM. BioMechanics vol. CII, No. 5, May 2005.

Osteoarthritis and Cartilage; D. Garland, et al.; vol. 15, Issue 6, Jun. 2007, pp. 630-637.

International Search Report for International Application No. PCT/US2005/008010 (4 Pages) I.E. WO 2005/087148 listed above. (dated May 7, 2005).

Pulsed Electrical Stimulation to Defer TKA in Patients With Knee Osteoarthritis from Orthopedics Oct. 1, 2006; by M.A. Mont, et al., published in http://www.orthosupersite.com/view.aspx?rid=18717—printed on May 18, 2010.

Farr, Jack, et al., Pulsed Electrical Stimulation in Patients With Osteoarthritis of the Knee: Follow Up in 288 Patients Who Had Failed Non-Operative Therapy, 2006, pp. 227-233, Orthopaedic Surgery, Surgical Technology International XV, Universal Medical Press, Inc., San Francisco, CA.

O'Driscoll SW., et al., Durability of regenerated articular cartilage produced by free autogenous periosteal grafts in major full-thickness defects in joint surfaces under the influence of continuous passive motion. A follow-up report at one year. J Bone Joint Surg Am. Apr. 1988;70(4):595-606.

O'Driscoll SW, et al., The chondrogenic potential of free autogenous periosteal grafts for biological resurfacing of major full-thickness defects in joint surfaces under the influence of continuous passive motion. An experimental investigation in the rabbit. J Bone Joint Surg Am. Sep. 1986;68(7):1017-1035.

O'Driscoll SW, et al., The repair of major osteochondral defects in joint surfaces by neochondrogenesis with autogenous osteoperiosteal grafts stimulated by continuous passive motion. An experimental investigation in the rabbit. Clin Orthop Relat Res. Jul. 1986;(208):131-140.

O'Driscoll SW, et al., A method for quantitative analysis of ratios of types I and II collagen in small samples of articular cartilage. Anal Biochem. Mar. 1985;145(2):277-285.

O'Driscoll Sw, et al., The induction of neochondrogenesis in free intra-articular periosteal autografts under the influence of continuous passive motion. An experimental investigation in the rabbit. J Bone Joint Surg Am. Oct. 1984;66(8):1248-1257.

Salter RB. The physiologic basis of continuous passive motion for articular cartilage healing and regeneration. Hand Clin. May 1994;10(2):211-219.

Salter RB, et al., The protective effect of continuous passive motion on living articular cartilage in acute septic arthritis: an experimental investigation in the rabbit. Clin Orthop Relat Res. Sep. 1981;(159):223-247.

Salter RB, et al., The biological effect of continuous passive motion on the healing of full-thickness defects in articular cartilage. An experimental investigation in the rabbit. J Bone Joint Surg Am. Dec. 1980;62(8):1232-1251.

PCT International Search Report and Written Opinion (PCT/US2005/008010) dated Jun. 22, 2005 (11 pages).

(56) References Cited

OTHER PUBLICATIONS

PCT Notification of Transmittal of the International Preliminary Report on Patentability (PCT/US2005/008010) dated Jun. 12, 2006 (6 pages).
PCT Written Opinion of the International Preliminary Examining Authority (PCT/US2005/008010) dated Mar. 27, 2006 (7 pages).
International Application No. PCT/US2010/035206 International Search Report and Written Opinion of the International Searching Authority Dated July 21, 2010 Attached to International Publication No. WO 2010/135288—Nov. 25, 2010. (13 Pages).
International Application No. PCT/US2010/049602 International Search Report and Written Opinion of the International Searching Authority Dated November 17, 2010 Attached to International Publication No. WO 2011/037898—Mar. 31, 2011. (11 Pages).
International Application No. PCT/US2011/023200 International Search Report and Written Opinion of the International Searching Authority Dated March 17, 2011. (10 Pages).
Canadian Application No. 2558431; Office Action Dated Aug. 1, 2011. (3 Pages).
International Application No. PCT/US2012/048625 International Search Report and Written Opinion of the International Searching Authority Dated Oct. 9, 2012. (14 Pages).
J. Timothy Harrington, M.D., et al.; New Options for Treating Osteoarthritis of the Knee; A Supplement to Rheumatology News; November 2011: pp. 1-15; International Medical News Group, LLC, an Elsevier Company.
EPO Application No. EP11783886; European Patent Office Supplementary European Search Report Dated Oct. 16, 2013 (8 Pages).
EPO Application No. EP10778238; European Patent Office Supplementary European Search Report Dated Jul. 18, 2014 (6 Pages).
Singapore Application No. 201207877-0; Hungarian Intellectual Property Office Written Opinion Dated Apr. 5, 2014 and Invitation to Respond to Written Opinion Dated July 8, 2014 (10 Pages).
EPO Application No. EP12817188; EPO Communication Dated May 13, 2015 and Attached European Patent Office Supplementary European Search Report Dated May 5, 2015 (7 Pages).

* cited by examiner

Basic Use Screens

1. Main Display Screen

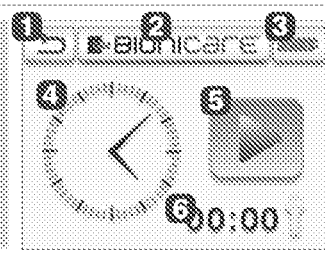

1. Back Button (press to return to previous screen)
2. Menu Button (press to advance to settings menu)
3. Battery Level (press for full screen reading)
4. Clock
5. Start Button (press to set voltage and begin treatment)
6. Usage time

2. Voltage Setting Screen

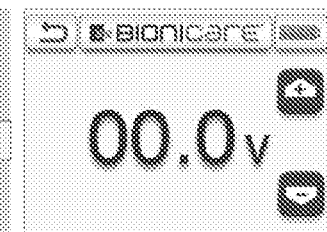

- Increase Button (press to increase voltage)
- Decrease Button (press to decrease voltage)
- *Quick Tip: Navigation buttons may also be used to adjust voltage*
- 00.0 v  Voltage from 00.0 to 12.0

3. Treatment Running Screen

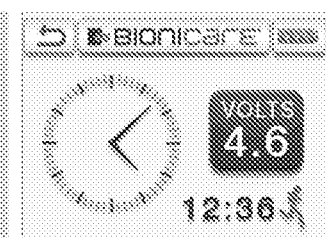

- 4.6  Voltage (press to adjust voltage)
- 12:36  Usage time (press for full screen reading)
- Running indicator 4. Locked Mode Screen

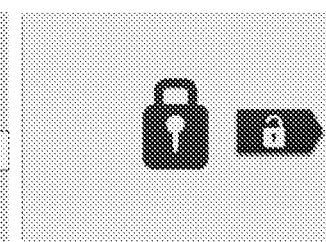

- Unlock button (press to unlock)
- *Quick Tip: Select button may also be used to unlock*

FIG. 11

Basic Use Screens

5. Settings Menu Screen

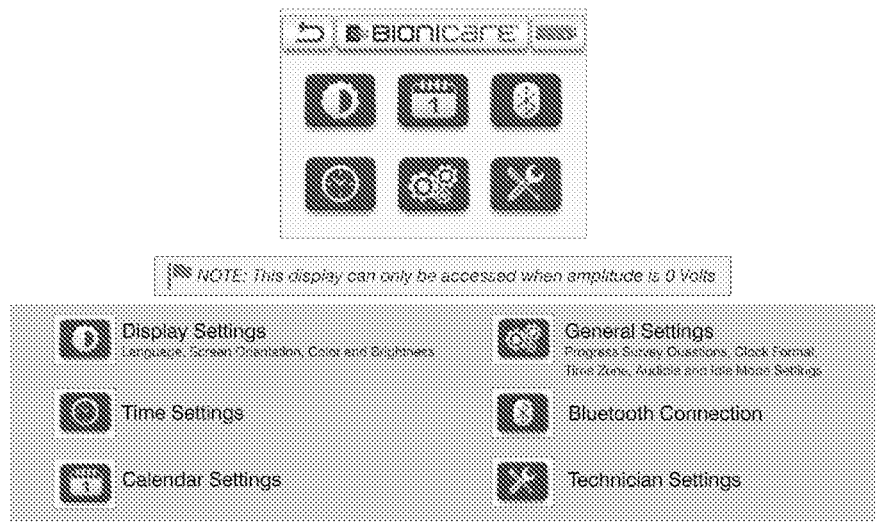

Understanding Special Display Messages
Special messages may appear on the display screen during use to report a low battery condition or other operational conditions that require attention.

Low Battery: When the device determines the battery is approaching the end of its usable charge, the device will continue to operate but the battery icon on the main display screen will flash and audible beep will sound. When this occurs, recharge the battery or replace it with a freshly charged battery.

Open (circuit): An "Open" circuit message will be displayed and an audible beep will sound if 1) the lead wire is disconnected from the generator ("Open" does not flash in this case) or 2) an electrode either loses skin contact or the wire is disconnected ("Open" will flash in these cases).

Advance Device Functions
The BioniCare Signal Generator has data recording and Bluetooth communication capabilities to allow it to capture patient data input and transmit it automatically to the BioniCare website. The patient can then access the website to see how their progress compares to that of all other BioniCare users. For information and instructions for the website, go to www.bionicare.com.

FIG. 12

ELECTROSTIMULATION SYSTEM

CROSS REFERENCE TO RELATED APPLICATIONS

This application claims the benefit of U.S. Provisional Application Ser. No. 61/512,402 filed Jul. 27, 2011, entitled Electrostimulation and Conductive Garment Improvements, the entire contents of which are hereby incorporated by reference. This application also claims the benefit of U.S. Provisional Application Ser. No. 61/576,342 filed Dec. 15, 2011, entitled Electrostimulation System, the entire contents of which are hereby incorporated by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND

1. Field of the Invention

The present field relates to electrostimulation for the promotion of joint health.

2. Description of Related Art

As discussed here, orthotic devices (orthoses) include any brace, splint, support, or other joint stabilizing means applied to any part of the body to protect, support, or treat biomechanical conditions. Orthotic devices generally include a biomechanical support element that forms the basis of the skeletal or soft tissue support that is required for the majority of these devices.

Orthotic devices must engage effectively with soft tissue in order to provide the desired support. In many parts of the body the soft tissue will move, for example by expanding or contracting as result of muscle or joint movement. For example, the objective of a rigid knee brace is to exert a force on the tibia with respect to the femur in the user's body mass above the knee. By definition, knee braces are applied to soft tissue lying between the brace and the user's skeleton. The rigid element may include some form of liner that contacts the body of the user. The liner may have an outer fabric that is designed to contact the user's skin directly or, alternatively, to engage with clothing that a user may be wearing about the part of the anatomy to which the orthotic device is to be attached. Soft tissue is mobile and in the case of the leg, moves in a cycle corresponding to a user's gait, whether it be through running, walking or other physical movement common to the human knee. The most mobile soft tissue is the quadriceps mechanism lying in front of the femur in the anterior thigh region. The central reference point for a knee brace is the knee joint line. In construction, an orthotic device such as a knee brace would use a joint mechanism, which mimics the movement of the joint to be supported, such as the knee, which is not just a simple hinge. Since each user's body shape is unique, the interface between the orthotic device and the user's leg cannot be predetermined in the manufacture of such a device. This technology can be applied to any brace or support on the body. The knee brace is simply used as an example.

Degenerative joint disease, osteoarthritis, rheumatoid arthritis, repetitive motion, carpal tunnel, tendinitis, and other joint diseases or injuries may be treated through various methods of electrical stimulation. Surface electrical stimulation (SES) treats these conditions using sub-sensory electrical pulses. Other methods of electrostimulation include Transcutaneous Electrical Nerve Stimulation (TENS), Transcutaneous Electrical Stimulation for Arthritis (TESA), Neuromuscular Electrical Stimulation (NMES), Interferential Stimulation (IF), High Volt Galvanic Stimulation, High Volt Pulsed Current (HVPC), Electromagnetic and Pulsed Electromagnetic Field Stimulation, and Micro Current Electrical Stimulation.

When the active user wears an orthotic device with an electrical stimulation assembly attached, there are several potential issues to be solved or minimized. One of these issues is durability, especially in the harsh environment between the device and the user's anatomy. The active user will move, walk, run, jump, and sweat. The assembly's design must be robust to survive this activity. With regards to bodily fluids such as sweat, the electrode assembly attached to the user's anatomy must stay in place, and continue to function well. Current electrodes are very sticky, with no way to ventilate sweat through the assembly.

Electrodes must also peel easily from the anatomy (not accidentally from the electrode carrier) when the orthotic device is removed. When the electrode is ready to be replaced, it must peel relatively easily from its electrode carrier, while not delaminating under normal use. It can be seen that there must be a careful, functional balance in designing the various adhesion layers. With regards to activity levels, current designs include a long wire leading from the signal generator to the electrode worn by the user. This wire can tangle, snag, pull out, and ultimately break electrical connection with the signal generator. The need exists to improve this assembly to a more robust design.

Sufferers of osteoarthritis of the knee or rheumatoid arthritis of the hand are in need of enhanced nondrug, non-invasive treatment.

BRIEF SUMMARY

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this Brief Summary, which is included for purposes of illustration only and not restriction.

In one aspect, for example, an electrostimulation system of the invention comprises or consists essentially of a signal generator, a docking assembly, and at least one transmission assembly. The signal generator is configured to produce at least one signal. The docking assembly includes a main housing; at least one mechanical retaining element operatively connected to the main housing that mechanically secures the signal generator to the docking assembly; and, at least one electrical docking element mechanically connected to the main housing that electrically connects the docking assembly to the signal generator. The at least one transmission assembly is adapted to fit on a portion of a user's anatomy, comprising at least one transmission assembly connection element (TACE) adapted to transmit a signal from the docking assembly to the user. The signal generator is electrically and mechanically detachably connected to the docking assembly during use.

In another aspect, for example, an electrostimulation system of the invention comprises or consists essentially of a signal generator, a docking assembly, and at least one transmission assembly, with the signal generator configured to produce at least one signal and the docking assembly adapted to secure the signal generator. The docking assembly includes a main housing; at least one electrical docking element mechanically connected to the main housing for electrical connection of the docking assembly to the signal generator; and at least one docking assembly connection element (DACE). The at least one transmission assembly adapted to fit on a portion of a user's anatomy, comprising at least one transmission assembly connection element (TACE) adapted to contact the DACE. At least one of either the DACE or TACE are disposed in locations that prevent signal transmission if the docking assembly is incorrectly assembled to the at least one transmission assembly.

In another aspect, an electrostimulation system of the invention comprises or consists essentially of, for example: a signal generator configured to produce at least one signal; and, at least one transmission assembly adapted to fit on a portion of a user's anatomy and transmit said at least one signal from said signal generator to the user. The at least one transmission assembly is adapted to be conductive in at least one selected area of treatment on the portion of the user's anatomy and insulative in other areas. The transmission assembly or assemblies may also be conductive, or adapted to be conductive, in more than one area of a user's anatomy. Additionally, the transmission assembly or assemblies may be conductive, or adapted to be conductive, in more than one area of a user's anatomy and insulative in one or more other areas of the user's anatomy.

In another aspect, for example, an electrostimulation system of the invention comprises or consists essentially of a signal generator comprising a main casing, at least one mechanical retaining element, at least two electrical connection elements, data connection means, at least one discrete physical button, an interactive display (for example, a touch screen display), and a user interface system (for example, an interface system that is, in whole or in part, a physically- or voice-controlled interface system). The main casing includes on or within it (or both) signal generator electronics configured to produce at least one signal for the promotion of joint health. The at least one mechanical retaining element is configured to mechanically secure the main casing to a docking assembly. The at least two electrical connection elements are operatively connected to the main casing for transmitting the signal. The data connection means is operatively connected to the main casing for transmission of electronic data. The at least one discrete physical button is operatively connected to the main casing for user input. The touch screen display is operatively connected to the main casing configured to function as a user interface. The user interface system is operatively connected to the touch screen display, and the interface system may be coded or programmed for displaying intuitive icons representing operational functions or status readouts on the touch screen display.

Examples of icons include treatment, signal output, signal input, data transmission, computer interface, data connection, docking status, server interface and treatment report icons. The user may also use physical buttons that may be included, for example, to access one or more or all of the same functions and/or icons.

In another aspect, for example, the invention is embodied as a signal generator comprising a main casing, at least one mechanical retaining element, at least two electrical connection elements, data connection means, at least one discrete physical button, a touch screen display, a user interface system, and wireless data transmission means. The main casing has signal generator electronics configured to produce at least one signal for the promotion of joint health. The at least one mechanical retaining element is configured to mechanically secure the main casing to a docking assembly. The at least two electrical connection elements are operatively connected to the main casing for transmitting the signal. The data connection means is operatively connected to the main casing for transmission of electronic data. The at least one discrete physical button is operatively connected to the main casing for user input. The touch screen display is operatively connected to the main casing configured to function as a user interface. The user interface system is operatively connected to the touch screen display, and the interface system may be coded or programmed for displaying intuitive icons representing operational functions or status readouts on the touch screen display. Icons may include, for example, those listed or referenced herein. The wireless data transmission means provides two-way communication of data between the signal generator and an external system. One or more computers or other devices with a CPU or microprocessor useful for data transmission may also be used to assist in and/or as a conduit for communication between the signal generator and an external system.

In another embodiment, the signal generator can communicate with at least one additional external system.

The inventions include methods of using the electrostimulation system and signal generator device for prophylactic and therapeutic treatments to promote joint health, including for the treatment of arthritis (including for example rheumatoid arthritis and osteoarthritis).

The inventions also include kits comprising or consisting essentially of one or more electrostimulation systems, with instructions for use and/or with reference to a source of instructions for use (e.g., instructions available on the Internet). Articles of manufacture are also provided, comprising a package containing one or more electrostimulation systems, as described and/or claimed herein and instructions for use for the treatment of a subject. For example, an article of manufacture, comprises an electrostimulation system and instructions for use for the treatment of a subject suffering from diminished joint function, or who would otherwise benefit from electrostimulation to promote joint health.

The inventions also include kits comprising or consisting essentially of one or more signal generators, with instructions for use and/or with reference to a source of instructions for use (e.g., instructions available on the Internet). Articles of manufacture are also provided, comprising a package containing one or more signal generators, as described and/or claimed herein and instructions for use for the treatment of a subject. For example, an article of manufacture comprises a signal generator and instructions for use for the treatment of a subject suffering from diminished joint function, or who would otherwise benefit from electrostimulation to promote joint health.

BRIEF DESCRIPTION OF THE DRAWINGS

The present inventions, in accordance with one or more various embodiments, are described in detail with reference to the following figures. The drawings are provided for purposes of illustration only and merely depict some examples and/or embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

FIG. 11 illustrates display screens from an example of a signal generator, with display descriptions, as used for example in an operator's manual.

FIG. 12 illustrates further display screens from the example of a signal generator, with display descriptions, as used for example in an operator's manual.

Figure 1:
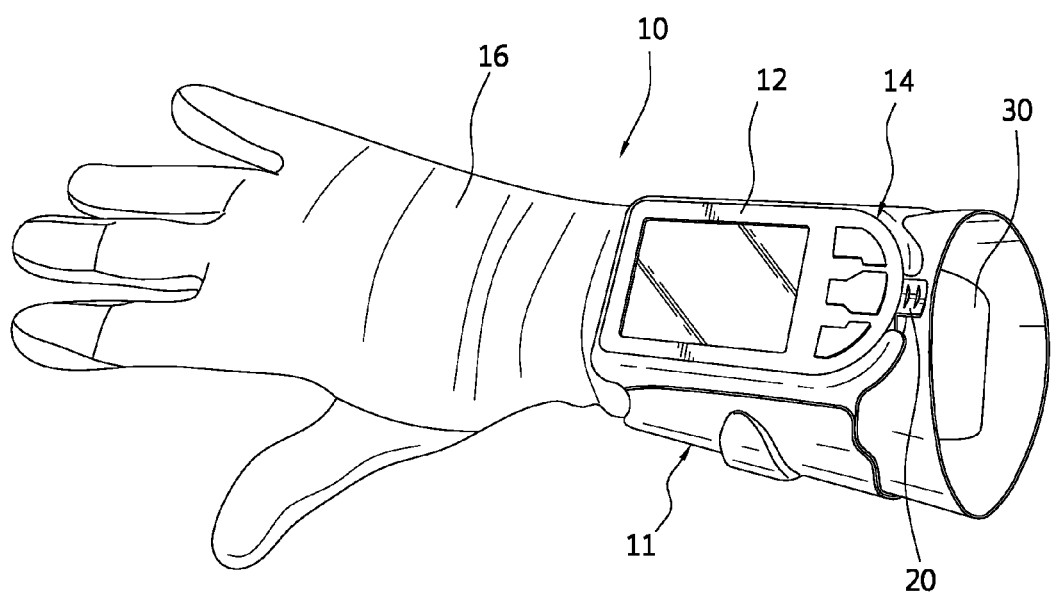
FIG. 1 is a perspective view of the dorsal side of one embodiment of the invention.
Figure 2:
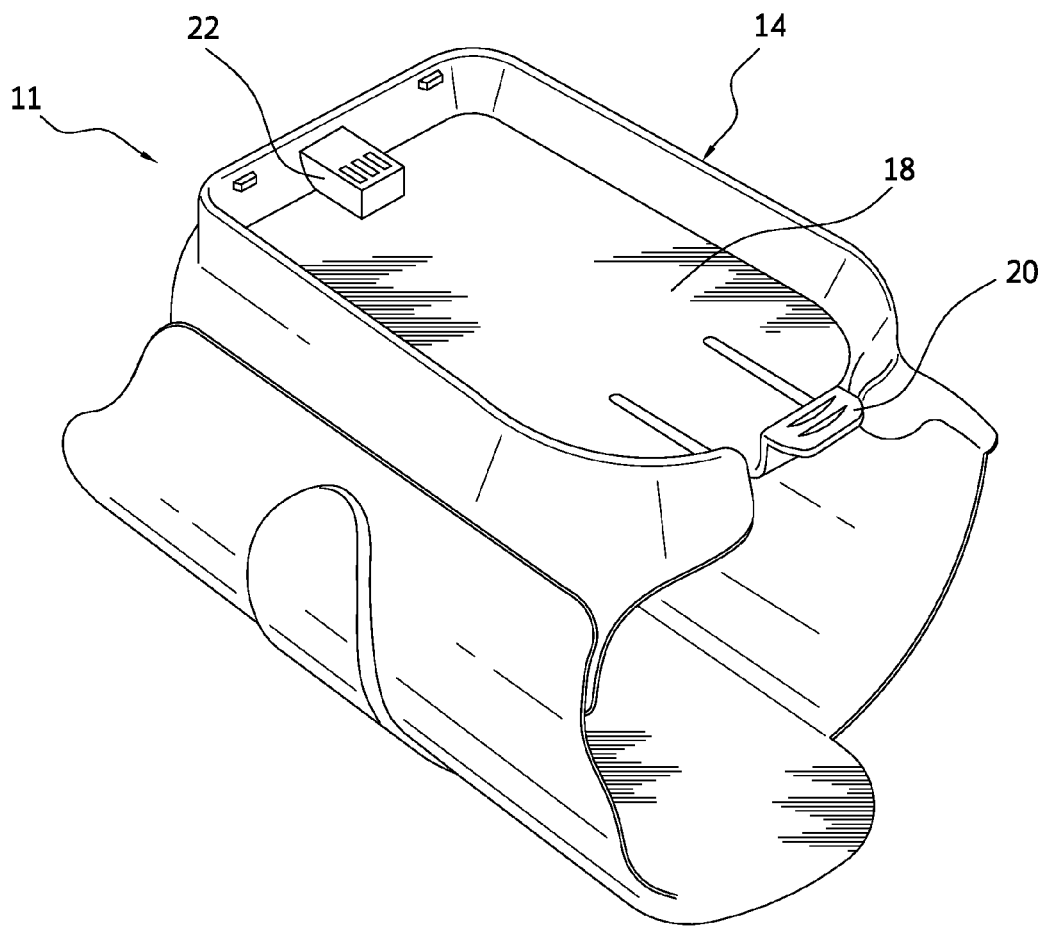
FIG. 2 is a perspective view of a docking assembly of the present invention.

The figures are not intended to be exhaustive or to limit the invention to the precise form disclosed. It will be understood that the invention can be practiced with modification and alteration, and modified and alternative component parts, and that the invention be limited only by the claims and equivalents thereof.

DETAILED DESCRIPTION

Referring now to the drawings and the characters of reference marked thereon FIGS. 1-4 illustrate one example of an electrostimulation system, designated generally as 10. In this broad aspect of the invention, the electrostimulation system 10 comprises a signal generator 12, a docking assembly, designated generally as 14, and at least one transmission assembly 16. The signal generator 12 is configured to produce at least one signal. In a further embodiment, for example, the signal generator is configured to produce at least one signal for the promotion of joint health. This signal may be, for example as described in Hoffman U.S. Pat. No. 5,273,033 incorporated by reference herein in its entirety. In one embodiment, the docking assembly 14 includes a main housing 18, at least one mechanical retaining element 20, and at least one electrical docking element 22. The mechanical retaining element 20 is operatively connected to the main housing 18 to mechanically secure the signal generator 12 to the docking assembly 14. The electrical docking element 22 (shown by way of example in FIG. 2) is mechanically connected to the main housing 18 for electrical connection of the docking assembly 14 to the signal generator 12. The docking assembly 14 is incorporated into a cuff 11 for attaching to a user's anatomy. In this instance the docking assembly 14 is shown as a wrist wrap. The transmission assembly is shown as an orthotic conductive glove 16.

As used herein, the term "signal generator" in one preferred embodiment refers to an electronic device that generates a repeating electronic signal in the analog domain. In other useful embodiments, the signal generator in an electrostimulation system as described and/or claimed herein may be selected from function generators, radio frequency and microwave signal generators, pitch generators, arbitrary waveform generators, digital pattern generators or frequency generators that are electronic devices that generate repeating or non-repeating electronic signals in either the analog or digital domains. Combinations of signal generators are also within the scope of the term "signal generator."

As used herein, "docking assembly" is broadly construed to include any item that can be used to secure signal generator 12, for example. Such items include but are not limited to: an orthotic device, wrap, belt, pants waistband, elastic waist band, arm wrap band, wrist wrap band, wrist gauntlet, glove, ankle wrap band, ankle wrap, knee brace, knee pull up, knee wrap band, sling, or other stable object and garments to secure the signal generator.

As used herein, "mechanical retaining element" is broadly construed to include any element that retains or secures the signal generator. Examples of such items include, but are not limited to: an undercut feature molded into the main casing, a belt-clip feature, a snap feature, a latch feature, a hook and loop fastener, such as Velcro®.

As used herein, the term "external system" refers to an application server configured to provide an interface to a server-based support system to authorized users, a resources server configured to securely store data, and a data transceiver (e.g. modem, or computer with Bluetooth® radio, etc.) configured to provide communication between the electrostimulation system and the external system. One example of an external system is disclosed in U.S. Ser. No. 12/541,796, filed on Aug. 14, 2009, entitled Interactive Electrical Stimulator Device and Server-Based Support System incorporated herein by reference in its entirety, as discussed above.

As used herein, "promote joint health," "promotion of joint health," or "promoting joint health," or the like refers to prophylactic and/or therapeutic support for or improvement of any of the tissues that make up an anatomical joint. Promotion of joint health, etc. includes, for example, the prophylactic and/or affirmative therapeutic treatment of degenerative issues, amelioration of pain, or other beneficial improvement(s) to the health or function of a joint or related structure.

The transmission assembly 16 is adapted to fit on a portion of a user's anatomy. In this embodiment, transmission assembly 16 also functions as an orthotic device, since it provides compression and some support to the anatomy. The orthotic device/transmission assembly 16 includes at least one transmission assembly connection element (TACE) 24 (see, for example, FIG. 4) which is adapted to transmit a signal from the docking assembly 14 to the user. A signal generator 12 is detachably secured to the docking assembly, achieving simultaneous mechanical and electrical connection.

The signal generator 12 may be designed to provide one or more signals that promote overall joint health. A preferred output signal is as described in Hoffman U.S. Pat. No. 5,273,033 and discussed above. Other output signals from the generator include, but are not limited to, Transcutaneous Electrical Joint Stimulation (TEJS) signals, and signals known as Transcutaneous Electrical Stimulation for Arthritis (TESA). Other signals that may be provided by the generator include, but are not limited to Surface Electrical Stimulation (SES) signals, Neuromuscular Electrical Stimulation (NES/NMES) signals, Interferential Stimulation (IS/IF) signals, High Volt Galvanic Stimulation (HVGS) signals, High Volt Pulsed Current (HVPC) signals, Electromagnetic and Pulsed Electromagnetic Field Stimulation (EFS and PEFS/PEMF) signals, and Micro Current Electrical Stimulation (MCES) signals. Still other signals that may be provided by the generator include signals known as Transcutaneous Electrical Nerve Stimulation (TENS).

The main housing 18 may be formed of, for example, molded plastic. The mechanical retaining element 20 is preferably integrally formed therewith.

The electrical docking element 22 may comprise or consist essentially of one or more contact springs such as those, for example, employed in cell phone or laptop batteries. Other embodiments include, for example, simple contact patches of conductive material or electrode wire connectors known in the medical industry.

The transmission assembly connection element (TACE) 24 is preferably formed of a conductive fabric, or other conductive material such as a material comprising or consisting essentially of a hydrogel. The conductive fabric may be constructed using, for example, a conductive hook or loop, commonly known as Velcro®. A conductive contact patch, metal rivet, or other fastening means can also be employed, for example.

The docking assembly further preferably includes at least one docking assembly connection element (DACE) 26 electrically connected or electrically connectable to a TACE 24. The DACE 26, by way of example, may be formed of the same material as TACE 24, as described above.

Figure 3:
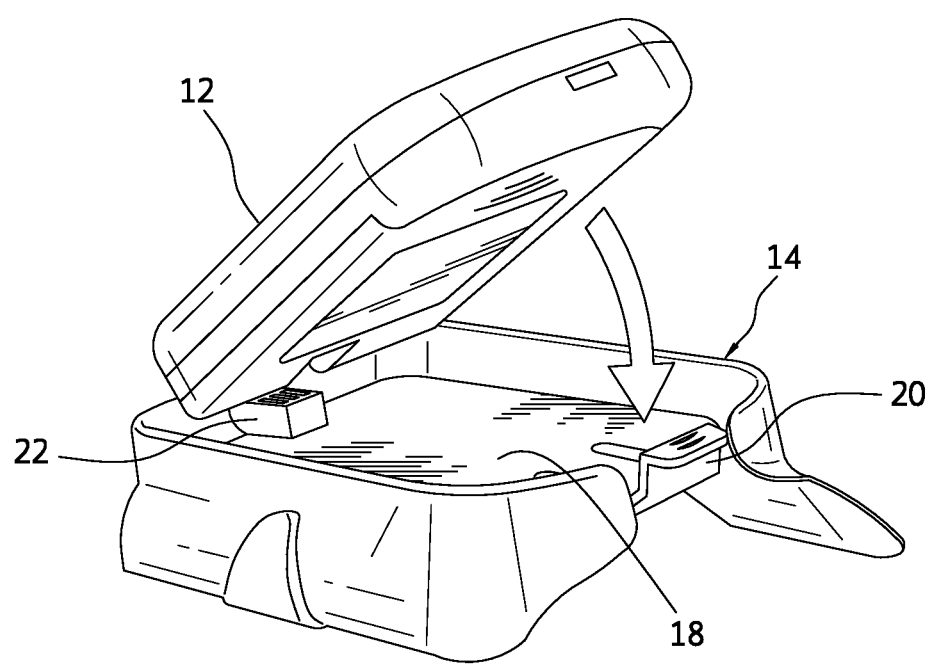
FIG. 3 is a perspective view of the signal generator of the present invention being secured into a docking assembly.

A signal generator 12 may be configured to snap into place during operation, as shown by way of example in FIG. 3, forming both the proper mechanical and electrical connection during use.

In this example of one embodiment of the inventions, the transmission assembly 16 is a glove. The glove may preferably, for example, be formed of elastic material for ease of donning on or application to the user's anatomy. Transmission assembly 16, for example, includes one or more signal conduits 25 that function to carry the signal from transmission assembly connection element (TACE) 24 to signal transmission elements 28. Signal conduits 25 can be made from conductive fabric, wire, or other conductive materials to carry the signal, and can be integrated as part of transmission assembly connection elements, signal transmission elements or conductors 28', 30'. (Signal transmission elements 28', 30' are discussed below in more detail below regarding FIG. 6). Transmission assembly 16, for example, also includes one or more signal transmission elements 28 and 30 that transmit the signal to the user's anatomy. In this example of one embodiment, "active" signal transmission elements 28 transmit the signal through the anatomy to one or more "dispersive" signal transmission elements 30. The signal transmission elements 28, 30 are affixed to or formed integral to the glove 16.

While the above account describes one embodiment, the inventions are adaptable to treat any portion of the user's anatomy including the following portions, for example: fingers, wrist, hand, elbow, shoulder, hip, knee, ankle, foot, and spine.

As described above, the example in FIG. 4 shows an embodiment whereby electrostimulation therapy can be targeted directly to one or more areas of treatment on the user's anatomy. Incorporating specific treatment areas in the design is further improved by insulating the treatment from accidental contact with the electrostimulation signal by the patient.

For example, current products on the market include those that are conductive on the entire surface area, inside and out. This is a potential hazard if the user touches other parts of their body or other conductive items during treatment, since the signal will transmit through whatever is being touched. For example, grasping a metal utensil and touching one's lips, or adjusting metal framed glasses causing conduction to an eye.

The transmission elements 28 and 30 may also be disposed, for example, in locations to limit pressure-points during use. These are locations where compressive pressures created by the user affecting acts of daily living might further compress the transmission elements against the user's anatomy causing the electrical impedance of the system to fall resulting in a sudden rise in signal transmission to the user. Such a sudden rise might lead to discomfort or a reflex reaction that could contribute to a harmful event, for example, dropping an object or knocking over an object.

This invention provides many novel embodiments that represent important and significant improvements over previous devices. Examples of such improvements include focusing treatment to targeted areas of the anatomy, while also preventing accidental transmission of the signal which could startle the user, possibly resulting in injury. Other significant features include, for example, a user interface with context-specific icons, a user-friendly touchscreen, and/or a navigation system, as described in further detail below. Still another aspect of note is the inclusion of components providing wireless functionality, including wireless data transmission to an external system, comprising one or more servers, with or without transmission via one or more computers and the like, as well as remote control from a wireless device linked to a signal generator, as described below. Yet another feature providing an advantage over the prior art is the novel construction of direct contact/direct transmission electrodes, eliminating the need for wires to be attached to the electrodes. Still other novel advantages are described below and elsewhere herein.

The importance of targeting specific areas of the anatomy for treatment—and excluding others—has been demonstrated in Finite Element Analysis (FEA) modeling and experiments. This FEA modeling helped to determine that a preferred location to dispose transmission elements 28 was at the fingertips, to force the signal through the entire joint, thereby improving the therapeutic effects of the treatment.

Figure 5:
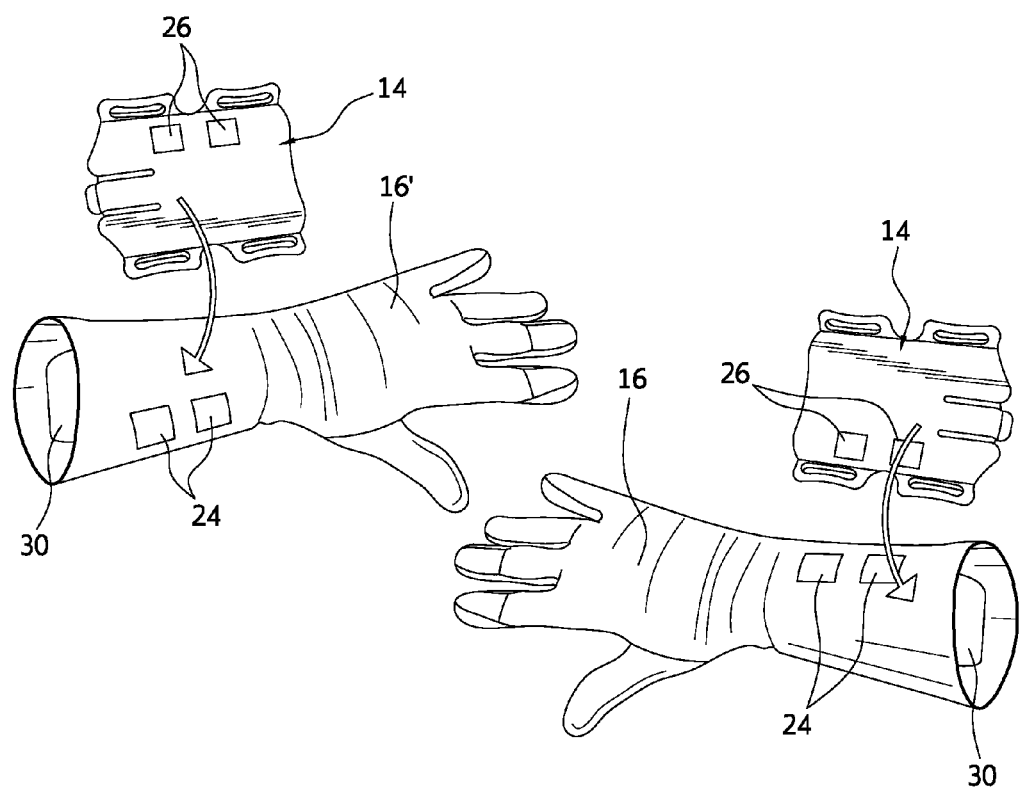
FIG. 5 is a perspective view of an example of one embodiment of the invention, showing an example of a cuff and docking assembly oriented on the Left and Right hand applications of an example of a transmission assembly.

In another broad aspect, FIG. 5 shows examples of transmission assemblies 16 and 16' in both Right-handed 16 and Left-handed 16' configurations. At least one TACE 24 is disposed in different locations on the Left versus the Right configuration. With this embodiment, DACE 26 on docking assembly 14 will only function if it is positioned correctly on the TACE 24 of the transmission assembly 16 or 16'. This prevents the docking assembly from being installed upside-down, and is especially useful in commonly seen bi-lateral applications when the patient is wearing the system on both hands.

Figure 4:
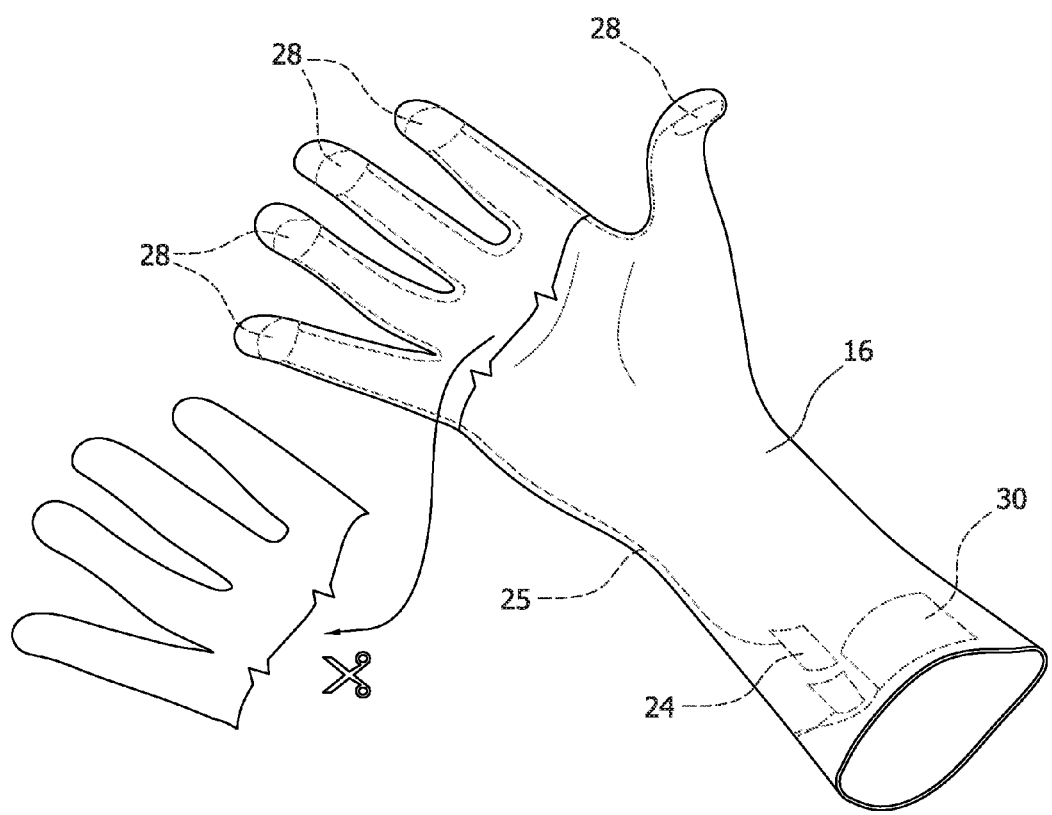
FIG. 4 is a perspective cutaway view of the palmar side of an example of a transmission assembly, showing one example of signal transmission elements.
Figure 6:
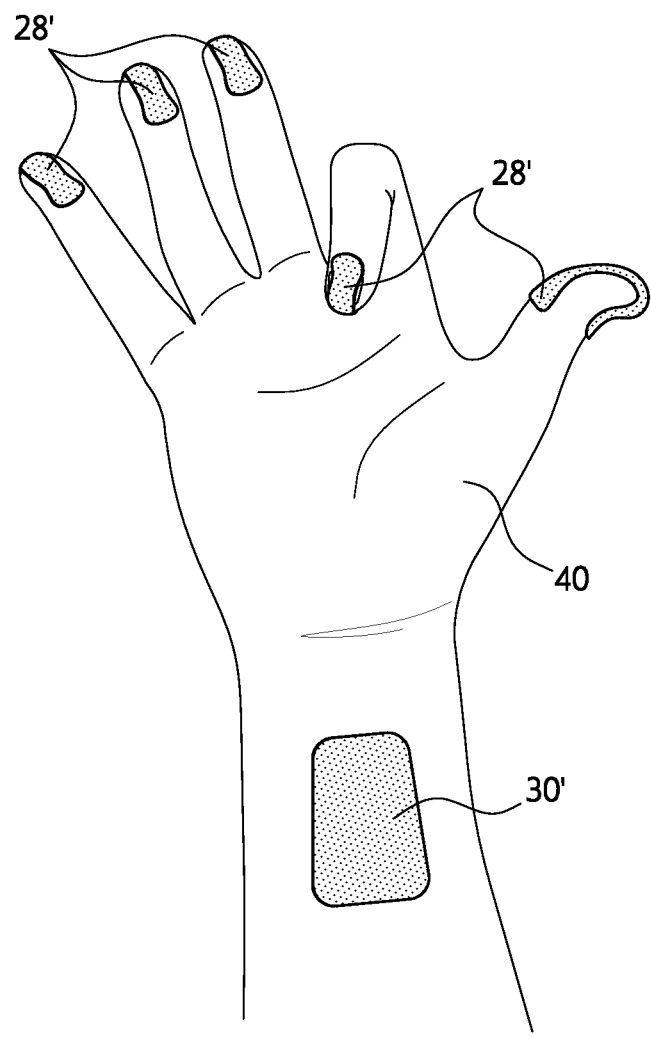
FIG. 6 is a perspective view of the palmar side of the right hand, showing a further example of one embodiment of the invention, with the glove removed for the purposes of clarity.

Referring now to FIG. 6, signal transmission elements, or active electrodes 28', are constructed of a conductive interface layer that adheres to the anatomy 40, and an outer conductive material layer that contacts other signal transmission elements 28 at the inner surface of the glove 16 (shown in FIG. 4). Conductive interface layer can be formed using hydrogel, for example. Conductive material layer can be formed using conductive fabric knitted or woven from materials including but not limited to, for example: silver, carbon, cotton, bamboo, lycra, spandex, nylon, or polyester and the like. Following the signal for this particular embodiment, there is a transmission path of, for example: signal generator 12, electrical docking element 22, docking assembly connection element (DACE) 26, transmission assembly connection element (TACE) 24, signal transmission element 28, signal transmission element (active electrode) 28', anatomy 40, signal transmission element (dispersive electrode) 30', signal transmission element 30, transmission assembly connection element (TACE) 24, docking assembly connection element (DACE) 26, electrical docking element 22, and signal generator 12.

Transmission assembly 16, TACE 24, and transmission elements 28, 28', 30, and 30' may be formed of materials, for example, that allow stretching during movement of the anatomy, such as conductive or non-conductive lycra, spandex, rubber, plastic, foam, neoprene, elastic, or similar materials. This aids fit and comfort in this embodiment when the fingers or wrist or other portions of the anatomy are bent/flexed, and has similar benefits when employed on any anatomical joint or area.

Figure 7:
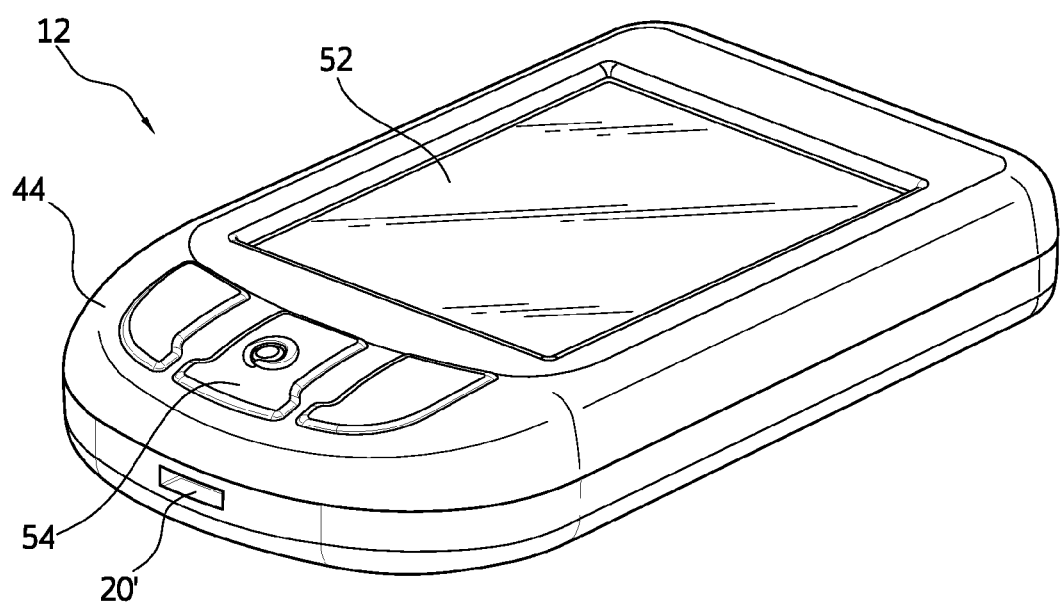
FIG. 7 is a perspective view of an example of one embodiment of the invention, showing the top side of an example of a signal generator.
Figure 8:
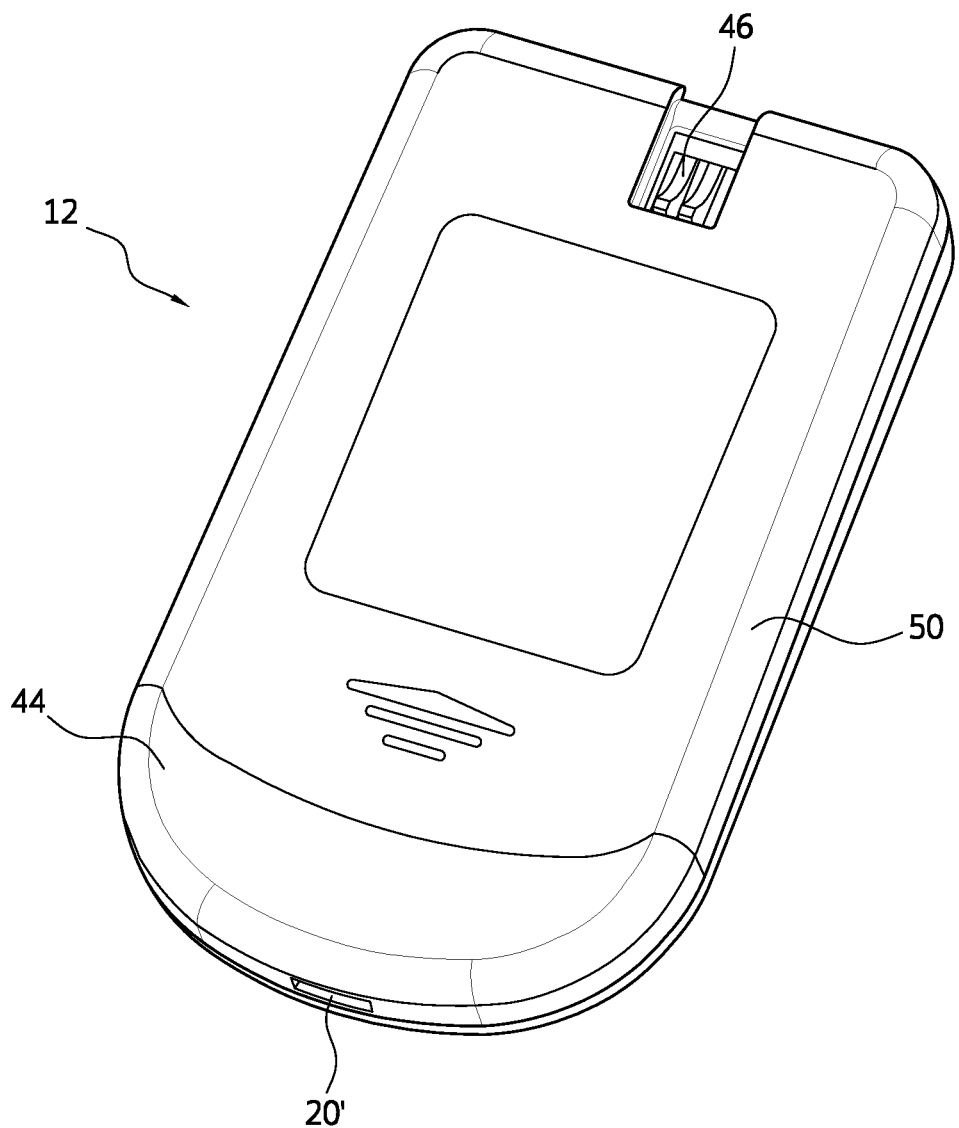
FIG. 8 is a perspective view of an example of one embodiment of the invention, showing the under-side of an example of a signal generator.

Referring to FIGS. 7 and 8, by way of example, signal generator 12 comprises or consist essentially of a main casing 44, touch screen 50 and at least one discrete (physical) button 54, at least one electrical connection element 46, and mechanical retaining element 20'. In this embodiment, mechanical retaining element 20' is the mate to mechanical retaining element 20 located on the docking assembly 14. This embodiment shows 3 physical buttons that can be used instead of the touch screen for most if not all device operations. Ease of use is another advantage in this example, since either the touchscreen, or the discrete buttons, or a combination of both can be utilized by the user for optimal or desired functionality. In this embodiment, there are three discrete buttons: "UP", "DOWN", and "ENTER". These are used to select, then choose settings such as signal power, voltage, treatment time, duty-cycle, language, screen brightness, screen orientation, etc. In the case of a multi-modality device, for example, a device that provides more than one signal or more than one type of signal, the buttons can also be used to choose which modality/modalities to provide treatment.

The buttons may be uniquely shaped with a soft-touch feel. The center button may include a raised area to facilitate tactile orientation by the user without needing to view the device.

Figure 9:
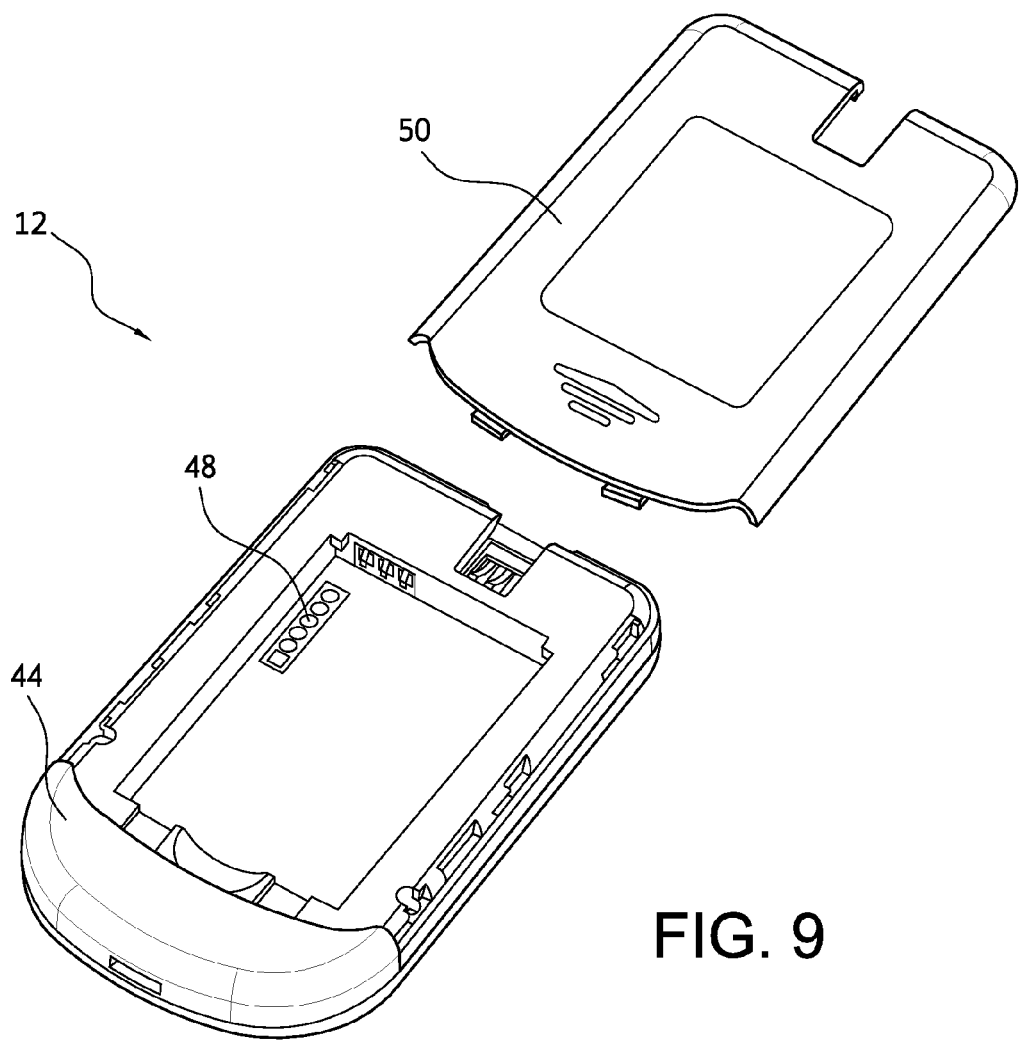
FIG. 9 is a perspective view of an example of one embodiment of the invention, showing the under-side of an example of a signal generator, with a battery cover removed.
Figure 10:
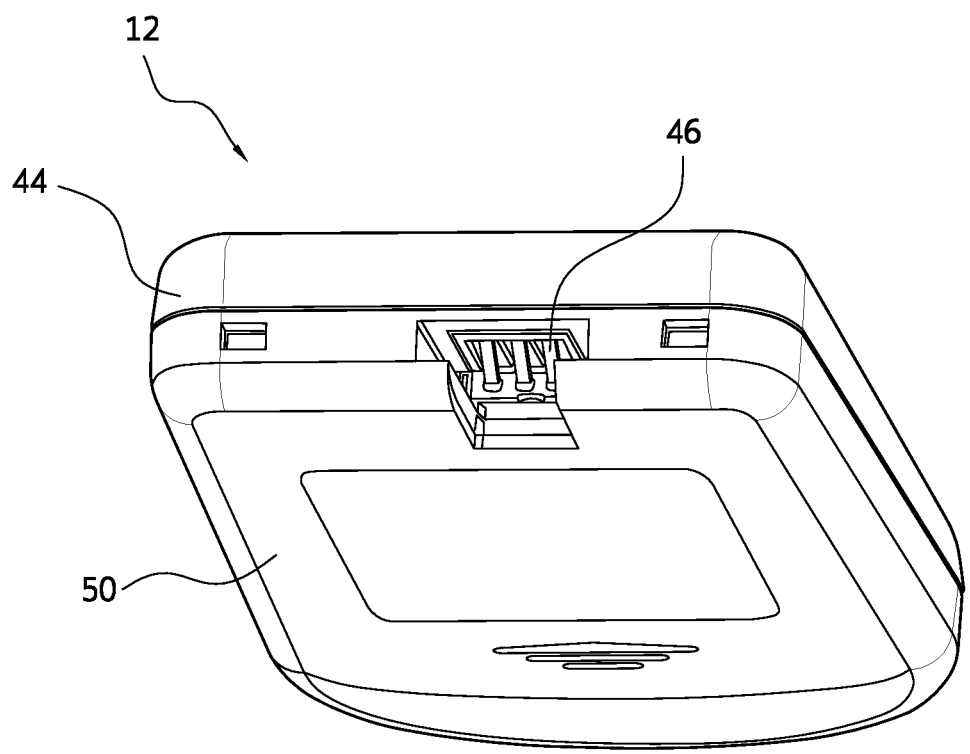
FIG. 10 is a perspective view of an example of one embodiment of the invention, showing the side of an example of a signal generator.

Referring to FIG. 9, the signal generator device in this example of one embodiment also includes data connection means 48 used to transmit data to or from the device, or to program the device when connected to a "bed-of-nails" or other similar programming apparatus. Such operations as manufacturing validation, final functional software upload, firmware updates, programming instructions, or patient data can be transmitted to or from the signal generator via data connection means 48. In the example of FIG. 10 a plurality of electrical connection elements 46 is shown.

Referring to FIGS. 11 and 12, examples of screens are shown from the signal generator's user interface. This user interface is designed to efficiently communicate information to the user, and easily allow the user to navigate and input data. This is done by intuitive icons that are context-specific. For example, the "person" icon shown in FIG. 11, "1. Main Display Screen" and "3. Treatment Running Screen" changes from standing to running when treatment is being delivered. If the user wishes to check battery life, he simply touches the battery icon shown as item 3 in "1. Main Display Screen". Voltage adjustment "UP" or "DOWN" can be controlled with either touch screen arrows or discrete physical buttons arranged pointing "UP" or "DOWN". This not only allows for easy navigation and use of the device, it also reduces risk of misuse, especially if the user does not refer to the instructions for use. (BioniCare® is the registered trademark of the Assignee of the present invention.)

Thus, as explained above, the present invention does not require the user to plug in discrete wires and connectors to interface with the signal generator. Instead, the present invention provides automatic connection.

Figure 13:
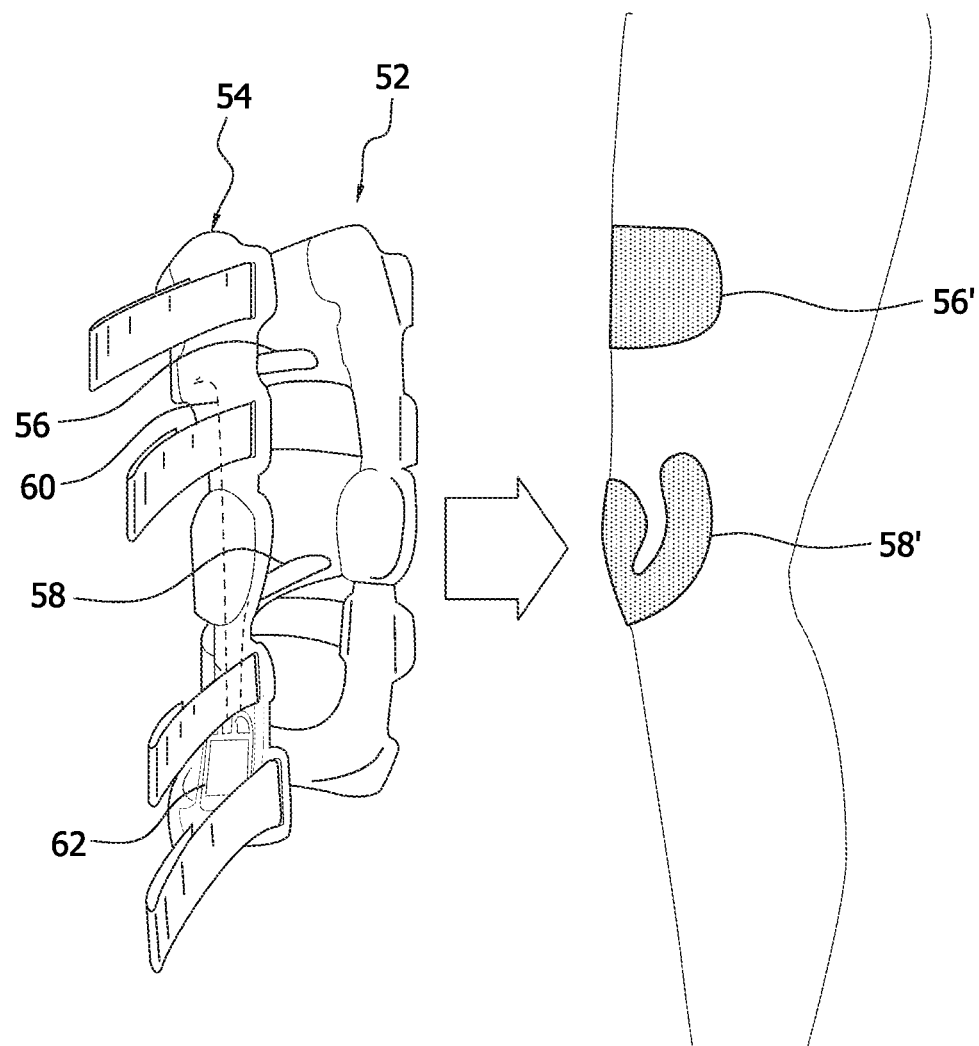
FIG. 13 illustrates another embodiment of the electrostimulation system, shown as embodied as a knee orthotic device.
Figure 14:
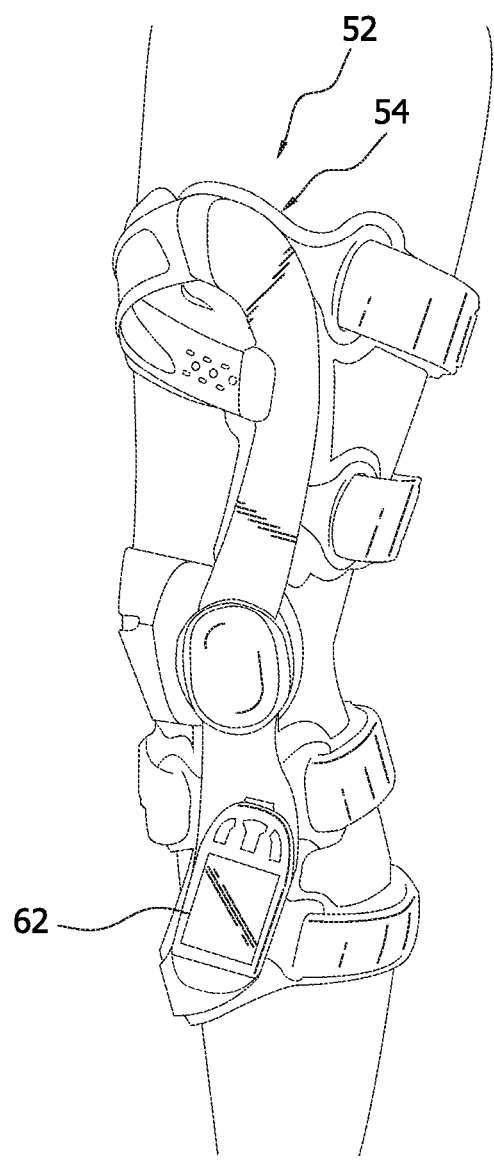
FIG. 14 illustrates the embodiment of FIG. 13 secured to the leg of the user.

FIGS. 13 and 14 show another embodiment of the electro-stimulation system, designated generally as 52, used to treat a knee joint. Orthotic device/transmission assembly 54 is shown as a knee brace integrated with the signal generator 12. Other types of knee orthoses may be utilized such as a knee wrap or knee pull up.

The transmission assembly 54 comprises a knee orthotic device including a plurality of signal transmission elements 56, 56', 58, 58'. The signal transmission elements include an active signal transmission element 58 preferably being positioned at a knee joint location on a surface of said knee orthotic device and at least one dispersive transmission element 56 spaced from the knee joint location. Transmission assembly 54, for example, includes one or more signal conduits 60 that function to carry the signal from the signal generator 62 to the signal transmission elements 56, 58.

In this embodiment, the DACE is an integral part of the transmission assembly 54. Signal transmission elements 56 and 58 collectively comprise the TACE. The TACE 56,58 comprise conductive fabric or other conductive material positioned on the knee orthotic device 54 to electrically connect to the signal transmission elements 56' and 58' positioned on the user's anatomy.

As in the hand embodiment, this knee embodiment does not require the user to plug in discrete wires and connectors to interface with the signal generator. Instead, the present invention provides automatic connection. This is also the case when these inventive concepts are applied to other parts of the anatomy.

Other safety and convenience features that may be included are, for example, a low battery tone, an open-circuit tone if the circuit is broken, and a lock screen to prevent unintentional changes to operating parameters.

Materials used will typically be high-strength, appropriate to resist impacts. Power for the device may be provided by at least one rechargeable battery or disposable battery, or other power sources, with or without external connections for power or recharging.

In a further embodiment, a signal generator 12 is also equipped or associated with wireless communications to allow data transmission and programming wirelessly. This can be accomplished via an on-board Bluetooth®, ZigBee®, or similar or other radio transceiver communicating with a nearby computer or wireless device such as a mobile phone. The remote computer or wireless phone, for example, can communicate and even control the signal generator remotely. Data such as patient usage may be transmitted to a computer or wireless device, then to a server based support system for compiling and reporting. This data may then be presented to the patient, treating physician, or other party to monitor and encourage progress.

A remote wireless device (such as a smart phone, wireless computer or tablet, for example) may also have a dedicated custom application or "app" programmed and installed to control the signal generator remotely. This will allow the signal generator to be simplified and miniaturized by removing the screen, buttons and other components. The signal generator may then be embedded or integrated within a product such as an orthotic or other device for promoting joint health. Without the need to directly access a signal generator, the product may be worn and remotely operated conveniently below clothing or other apparel. The device will also optionally include an on-board failsafe to disable it in the event of an emergency, for example, a "killswitch" that is easily accessible through clothing by the user.

Other examples of embodiments include applications for animal use. For example the device may be configured to be worn on an animal and controlled remotely as described above. Several animals' signal generator devices may be managed by one remote wireless controller through unique identification means. This provides a convenient treatment program for large facilities where many animals are treated simultaneously.

By way of example, such embodiments may include components that are ruggedized for outdoor and large or small animal applications. For example, the casing may be toughened through the use of waterproof, high-strength, abrasion resistant materials to counter the abuses incurred by the animals and their environments.

The wireless connection may also, for example, be initiated by a passcode or encrypted for security. A clock icon may be include that displays current time and is automatically synched with the clock in a computer or wireless device, for example. An alternative feature includes self-synchronization with an atomic clock.

Devices and systems of the invention will cater, for example, to elderly users who have medical conditions that hinder mobility, such as rheumatoid arthritis (RA) and osteoarthritis (OA), and other medical conditions. These users will especially benefit from embodiments configured to be intuitive, prevent or limit user mistakes, and promote ease-of-use.

Devices and systems of the invention will be used daily for the maximum number of hours tolerated by the user. Clinical studies such as those performed by Garland and Farr demonstrated a dose-dependent response in users. Daily use of such devices and systems may include the need to change or recharge batteries, or connect to some power source and upon each separate use, place signal transmission elements or conductors 28', 30' appropriately, and make adjustments to signal strength in accordance with operating instructions.

While specific embodiments of the invention have been shown in the drawings and described in detail it will be appreciated by those skilled in the art that various modifications and alternatives would be developed in light of the overall teachings of the disclosure. Accordingly, the particular arrangements disclosed herein are meant to be illustrative only and not limiting as to the scope of the invention, which is to be given the full breadth of the appended claims and in any and all equivalents thereof.

As mentioned above, although the present invention has been illustrated with respect to its implementation with a hand application, any part of the anatomy may use the present system and method. For example, the above described embodiments may be adapted to treat the foot, ankle, knee, hip, wrist, hand, elbow, spine, pelvis, or shoulder joints. "Adapted to treat" as used herein indicates that the signal and the system attributes may be worn, applied, or adjusted electrically and or physically to improve the efficacy of delivery of treatment to the particular area of the body. Examples of embodiments adapted to treat a foot, ankle, knee, hip, wrist, hand, elbow, spine, pelvis, or shoulder joints includes a sleeve, a glove, etc., any of which may be flexible and/or adjustable for fit and/or comfort.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to achieve the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it is understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present inventions are not limited by the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

Additional features of the present invention are shown and described in Appendix A attached hereto.

The inventions include methods of using the electrostimulation system to effect an efficacious prophylactic or treatment outcome and instructions for such use.

We claim:

1. An electrostimulation system comprising:
   a) a signal generator configured to produce at least one signal;
   b) a docking assembly comprising:
      i. a main housing;
      ii. at least one mechanical retaining element operatively connected to said main housing to mechanically secure said signal generator to said docking assembly; and,
      iii. at least one electrical docking element mechanically connected to said main housing for electrical connection of said docking assembly to said signal generator; and
   c) at least one transmission assembly adapted to fit on a portion of a user's anatomy, comprising at least one transmission assembly connection element (TACE) adapted to transmit a signal from said docking assembly to the user,
   wherein said signal generator is electrically and mechanically detachably connected to said docking assembly during use, and, wherein
      i. said at least one transmission assembly comprises a plurality of signal transmission elements, said plurality of signal transmission elements including a set of signal transmission elements being at selected anatomic locations at an inner surface of said transmission assembly and at least one other signal transmission element spaced from said anatomic locations;
      ii. said TACE comprises conductive fabric or other conductive material positioned on said transmission assembly and electrically connected to said signal transmission elements; and,
      iii. said docking assembly further comprises at least one docking assembly connection element (DACE) electrically connectable to said TACE so as to provide an electrical connection of said at least one docking assembly to said TACE.

2. The electrostimulation system of claim 1 wherein, said at least one transmission assembly comprises a conductive glove including said plurality of signal transmission elements, said plurality of signal transmission elements including said set of signal transmission elements being at said selected anatomic locations at an inner surface of said conductive glove, said anatomic locations being fingertip locations, said plurality of signal transmission elements including and at least one other signal transmission element spaced from said fingertip locations.

3. The electrostimulation system of claim 2 wherein said set of signal transmission elements comprises at least one active signal transmission element and at least one other signal transmission element comprises a dispersive signal transmission element.

4. The electrostimulation system of claim 3 wherein said at least one active signal transmission element is positioned on the fingertips and said at least one other dispersive transmission element is positioned on a forearm portion of the conductive glove.

5. The electrostimulation system of claim 1 wherein,
   said at least one transmission assembly comprises a knee orthotic device including said plurality of signal transmission elements, said plurality of signal transmission elements including at least one signal transmission element being positioned at a knee joint location and at least one other signal transmission element spaced from said knee joint location.

6. The electrostimulation system of claim 5 wherein said set of signal transmission elements comprises at least one active signal transmission element and at least one other signal transmission element comprises a dispersive signal transmission element.

7. The electrostimulation system of claim 1 wherein said signal generator, comprises:
   a) a main casing having signal generator electronics configured to produce at least one signal for the promotion of joint health;
   b) at least one mechanical retaining element configured to mechanically secure said main casing to a docking assembly;
   c) at least two electrical connection elements operatively connected to said main casing for transmitting said signal;
   d) data connection means operatively connected to said main casing for transmission of electronic data;
   e) at least one discrete physical button operatively connected to said main casing for user input;
   f) a touch screen display operatively connected to said main casing configured to function as a user interface; and
   g) a user interface system operatively connected to said touch screen display, said interface system programmed for displaying intuitive icons representing operational functions or status readouts on said touch screen display.

8. The electrostimulation system of claim 7 wherein:
   a) said at least one discrete physical button comprises three physical buttons, comprising: "UP", "DOWN", and "ENTER";
   b) wherein settings are selectable, said settings including signal power; and,
   c) said touch screen display being configured to provide:
      i) a main display;
      ii) a power setting display;
      iii) a treatment running display;
      iv) a locked mode display; and,
      v) a settings menu.

9. The electrostimulation system of claim 1 adapted to treat any of the following portions of the user's anatomy: fingers, wrist, hand, elbow, shoulder, hip, knee, ankle, foot, spine.

10. The electrostimulation system of claim 1 wherein said signal generator is controllable via a voice-controlled interface system.

11. The electrostimulation system of claim 1:
wherein said at least one transmission assembly is adapted to be conductive in at least one selected area of treatment on said portion of the user's anatomy and insulative in other areas.

12. The system described in claim 11, wherein said transmission assembly is insulative on an outer surface of said transmission assembly.

13. The electrostimulation system of claim 11, adapted to treat any of the following portions of the user's anatomy: fingers, wrist, hand, elbow, shoulder, hip, knee, ankle, foot, spine.

14. The electrostimulation system of claim 1, wherein at least one of either said DACE or TACE are disposed in locations that prevent signal transmission if said docking assembly is incorrectly assembled to said at least one transmission assembly.

15. The electrostimulation system of claim 1, wherein said electrostimulation system is part of a kit including a manual which includes clear text instructions which represent operating functions of said electrostimulation system.

16. The electrostimulation system of claim 1, wherein said signal generator comprises:
   a) a main casing having signal generator electronics configured to produce at least one signal for the promotion of joint health;
   b) at least one mechanical retaining element configured to mechanically secure said main casing to a docking assembly;
   c) at least two electrical connection elements operatively connected to said main casing for transmitting at least one signal;
   d) data connection means operatively connected to said main casing for transmission of electronic data;
   e) at least one discrete physical button operatively connected to said main casing for user input;
   f) a touch screen display operatively connected to said main casing configured to function as a user interface;
   g) a user interface system operatively connected to said touch screen display, said interface system programmed for displaying intuitive icons representing operational functions or status readouts on said touch screen display; and,
   h) wireless data transmission means for two-way communication of data between the signal generator and an external system.

17. The electrostimulation system of claim 1, wherein said signal generator comprises one or more external systems.

\* \* \* \* \*